(12) United States Patent
Schulman et al.

(10) Patent No.: US 6,695,885 B2
(45) Date of Patent: Feb. 24, 2004

(54) METHOD AND APPARATUS FOR COUPLING AN IMPLANTABLE STIMULATOR/SENSOR TO A PROSTHETIC DEVICE

(75) Inventors: Joseph H. Schulman, Santa Clarita, CA (US); Yitzhak Zilberman, Santa Clarita, CA (US); Lee J. Mandell, West Hills, CA (US)

(73) Assignee: Alfred E. Mann Foundation for Scientific Research, Valencia, CA (US)

( * ) Notice: Subject to any disclaimer, the term of this patent is extended or adjusted under 35 U.S.C. 154(b) by 0 days.

(21) Appl. No.: 10/002,370

(22) Filed: Nov. 15, 2001

(65) Prior Publication Data

US 2002/0198604 A1 Dec. 26, 2002

Related U.S. Application Data

(63) Continuation-in-part of application No. 09/677,384, filed on Sep. 30, 2000, now Pat. No. 6,564,807, which is a division of application No. 09/048,827, filed on Mar. 25, 1998, now Pat. No. 6,164,284, and a continuation-in-part of application No. 09/030,106, filed on Feb. 25, 1998, now Pat. No. 6,185,452.

(60) Provisional application No. 60/039,164, filed on Feb. 26, 1997, provisional application No. 60/042,447, filed on Mar. 27, 1997, and provisional application No. 60/300,397, filed on Jun. 22, 2001.

(51) Int. Cl.[7] .................................................. A61F 2/70
(52) U.S. Cl. ............................. 623/25; 623/24; 607/60
(58) Field of Search ............................. 623/24, 25, 57; 607/60, 61, 62, 65; 600/544, 545

(56) References Cited

U.S. PATENT DOCUMENTS

| | | | |
|---|---|---|---|
| 5,193,539 A | 3/1993 | Schulman et al. | |
| 5,193,540 A | 3/1993 | Schulman et al. | |
| 5,312,439 A | 5/1994 | Loeb | |
| 5,314,458 A | 5/1994 | Najafi et al. | |
| 5,314,495 A | 5/1994 | Kovacs | |
| 5,324,316 A | 6/1994 | Schulman et al. | |
| 5,358,514 A | 10/1994 | Schulman et al. | |
| 5,405,367 A | 4/1995 | Schulman et al. | |
| 5,877,943 A | 3/1999 | Ramamurthi | |
| 6,016,449 A | 1/2000 | Fischell et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,254,548 B1 | 7/2001 | Ishikawa et al. | |
| 6,261,247 B1 | 7/2001 | Ishikawa et al. | |
| 6,264,611 B1 | 7/2001 | Ishikawa et al. | |
| 6,266,567 B1 | 7/2001 | Ishikawa et al. | |
| 6,295,466 B1 | 9/2001 | Ishikawa et al. | |
| 6,315,721 B2 | 11/2001 | Schulman et al. | |
| 6,398,710 B1 | 6/2002 | Ishikawa et al. | |
| 6,415,184 B1 | 7/2002 | Ishikawa et al. | |
| 6,423,056 B1 | 7/2002 | Ishikawa et al. | |
| 6,447,448 B1 * | 9/2002 | Ishikawa et al. ............ 600/300 |
| 6,505,409 B2 | 1/2003 | Toda et al. | |
| 6,546,268 B1 | 4/2003 | Ishikawa et al. | |
| 6,546,291 B2 | 4/2003 | Merfeld et al. | |
| 2001/0001125 A1 | 5/2001 | Schulman et al. | |

* cited by examiner

*Primary Examiner*—Bruce Snow
*Assistant Examiner*—Cheryl Miller
(74) *Attorney, Agent, or Firm*—Lee J. Mandell; K. Cyrus Khosravi

(57) ABSTRACT

A system of implantable sensor/stimulation devices that is configured to communicate with a prosthetic device, e.g., an artificial limb, via a wireless communication link, preferably bidirectionally. By communicating between the implantable devices coupled to neural pathways within a man and motor/sensor interfaces in the prosthetic device, a machine, a man/machine interface is established to replace an absent limb. Systems of the present invention may extend to prosthetic devices, e.g., cranes or the like, that further extend the man/machine interface to allow a man to control a "large" remote piece of machinery directly via neural control.

37 Claims, 10 Drawing Sheets

FIRST ALTERNATIVE PROSTHETIC APPLICATION

OPEN LOOP CONTROL/MONITOR

CLOSED LOOP CONTROL

EXEMPLARY INJURY

COORDINATED CLOSED LOOP HAND CONTROL

FIRST ALTERNATIVE PROSTHETIC APPLICATION

SECOND ALTERNATIVE PROSTHETIC APPLICATION

METHOD AND APPARATUS FOR COUPLING AN IMPLANTABLE STIMULATOR/SENSOR TO A PROSTHETIC DEVICE

This application is a continuation-in-part of U.S. patent application Ser. No. 09/677,384, filed Sep. 30, 2000, now U.S. Pat. No. 6,564,807, which in turn is a divisional of U.S. patent application Ser. No. 09/048,827, filed Mar. 25, 1998, now U.S. Pat. No. 6,164,284, which in turn claims the benefit of U.S. Provisional Application No. 60/042,447, filed Mar. 27, 1997, and a continuation-in-part of U.S. patent application Ser. No. 09/030,106, filed Feb. 25, 1998, now U.S. Pat. No. 6,185,452, which in turn claims the benefit of U.S. Provisional Application No. 60/039,164, filed Feb. 26, 1997. Furthermore, this application claims the benefit of U.S. Provisional Application No. 60/300,397, filed Jun. 22, 2001.

FIELD OF THE INVENTION

The present invention is generally directed to implantable medical devices and in particular battery-powered implantable medical devices and to prosthetic devices which communicate with such devices.

BACKGROUND OF THE INVENTION

The present invention generally relates to systems for monitoring and/or affecting parameters of a patient's body for the purpose of medical diagnosis and/or treatment. More particularly, systems in accordance with the invention are characterized by a plurality of devices, preferably battery-powered, configured for implanting within a patient's body, each device being configured to sense a body parameter, e.g., temperature, $O_2$ content, physical position, electrical potential, etc., and/or to affect a parameter, e.g., via nerve and/or muscle stimulation. Significantly, one or more such implantable devices are configured to communicate with a prosthetic device via a wireless communication link and thus the implantable devices control and/or are affected by the prosthetic device.

Commonly owned U.S. Pat. No. 6,164,284 entitled "System of Implantable Devices For Monitoring and/or Affecting Body Parameters" and U.S. Pat. No. 6,185,452 entitled "Battery Powered Patient Implantable Device", incorporated herein by reference in their entirety, describe devices suitable for injectable implantation within a patient's body, i.e., beneath a patient's skin, for performing various functions including: (1) stimulation of body tissue and/or sensing of body parameters, and (2) communicating between implanted devices and devices external to a patient's body. Typically, such implantable devices are no larger than about 60 mm long and 8 mm in diameter and preferably no larger than 60 mm long and 6 mm in diameter and include even smaller embodiments, e.g., 15 mm long with an O.D. of 2.2 mm (resulting in an I.D. of about 2 mm). Depending upon the ailment affecting the patient, it may be desirable to communicate with a number of different devices, e.g., from one to thousands, while maintaining an update rate, e.g., on the order of every 1 millisecond to every second, sufficient to control and/or monitor the body parameter(s) at issue. Such implantable devices are preferably powered using rechargeable batteries.

By using a system of devices as described in the '284 and '452 patents, systems can "replace" damaged neural pathways. The present invention is primarily directed to systems of one or more such implantable devices that additionally comprise a prosthetic device (e.g., an artificial limb that replaces an absent limb) that communicates with such implantable devices.

SUMMARY OF THE INVENTION

The present invention is directed to a system of implantable devices, preferably battery-powered, that monitor and/or affect parameters of a patient's body and interfaces to a prosthetic device, e.g., an artificial limb. Such a system is particularly useful in a system comprised of a system control unit (SCU) and one or more devices implanted in the patient's body, i.e., within the envelope defined by the patient's skin. Each such implanted device is configured to be monitored and/or controlled by the SCU via a wireless communication link.

In accordance with the invention, the SCU comprises a programmable unit capable of (1) transmitting commands to at least some of a plurality of implanted devices, (2) receiving data signals from at least some of those implanted devices, and (3) interfacing with a prosthetic device, e.g., an artificial limb, preferably via a wireless communication link. In accordance with a preferred embodiment, the system operates in closed loop fashion whereby the commands transmitted by the SCU are dependent, in part, on the content of the data signals received by the SCU (see U.S. Pat. Nos. 6,208,894 and 6,315,721, each of which is incorporated herein by reference in their entirety).

In accordance with an exemplary embodiment, each implanted device is configured similarly to the devices described in the commonly owned U.S. Pat. No. 6,164,284 and typically comprises a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. Wireless communication between the SCU and the other implanted devices can be implemented in various ways, e.g., via a modulated sound signal, an AC magnetic field, an RF signal, a propagated electromagnetic wave, a light signal, or electrical conduction.

In embodiments of the present invention, the system of implantable devices communicate with a prosthetic device, e.g., an artificial limb, preferably in a closed loop manner. Accordingly, a man/machine interface is established that extends one or more of a patient's operational neural pathways to provide direct control and/or input from a supplemental prosthetic device. In an exemplary embodiment, e.g., where the prosthetic device is an arm, an absent limb may be physically replaced by the prosthetic device which communicates via a wireless communication link with one or more of the implantable devices.

In a still further aspect of the present invention, the prosthetic device may be other than a replacement limb. For example, in a system where the prosthetic device is a remotely controlled machine, e.g., a robotic crane or the like, the machine may be remotely controlled by a user in response to normal neural stimuli sensed by one or more implantable devices.

The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention.

The present invention is directed to a system for monitoring and/or affecting parameters of a patient's body and more particularly to such a system comprised of a system control unit (SCU) and one or more devices implanted in a patient's body, i.e., within the envelope defined by the patient's skin. Each such implantable device is configured to be monitored and/or controlled by the SCU via a wireless communication link.

In accordance with the invention, the SCU comprises a programmable unit capable of (1) transmitting commands to at least some of a plurality of implanted devices, (2) receiving data signals from at least some of those implanted devices, and (3) interfacing with a prosthetic device, e.g., an artificial limb, preferably via a wireless communication link.

In accordance with a preferred embodiment, the system operates in closed loop fashion whereby the commands transmitted by the SCU are dependent, in part, on the content of the data signals received by the SCU (see U.S. Pat. Nos. 6,208,894 and 6,315,721, each of which is incorporated herein by reference in their entirety).

In accordance with a preferred embodiment, each implanted device is configured similarly to the devices described in the commonly owned U.S. Pat. No. 6,164,284 (hereinafter referred to as the '284 patent) and typically comprises a sealed housing suitable for injection into the patient's body. Each housing preferably contains a power source having a capacity of at least 1 microwatt-hour, preferably a rechargeable battery, and power consuming circuitry preferably including a data signal transmitter and receiver and sensor/stimulator circuitry for driving an input/output transducer.

Figure 1:
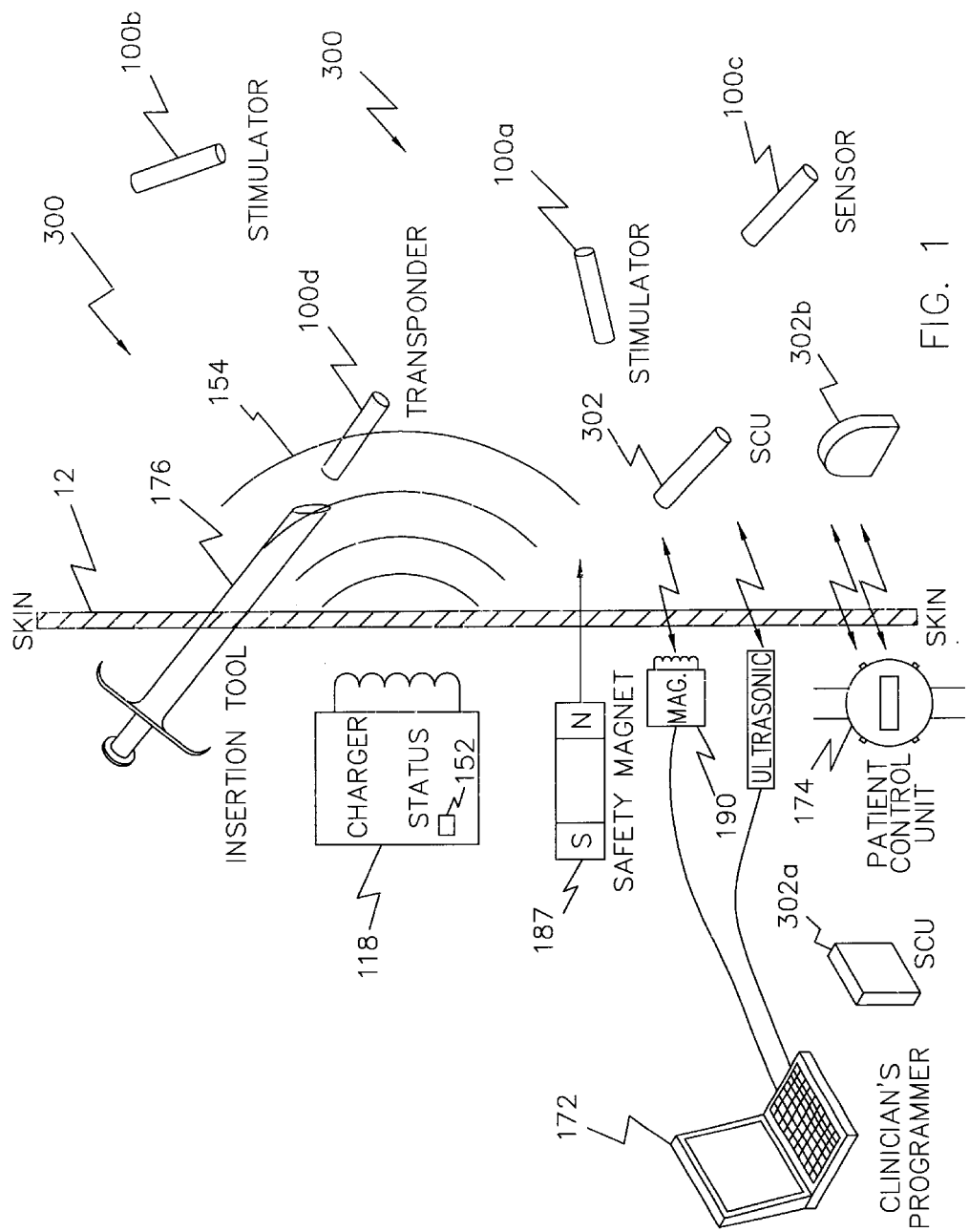
FIG. 1 is a simplified block diagram of an exemplary system suitable for practicing the communication protocol of the present invention, the system being comprised of implanted devices, e.g., microstimulators, microsensors and microtransponders, under control of an implanted system control unit (SCU).
Figure 2:
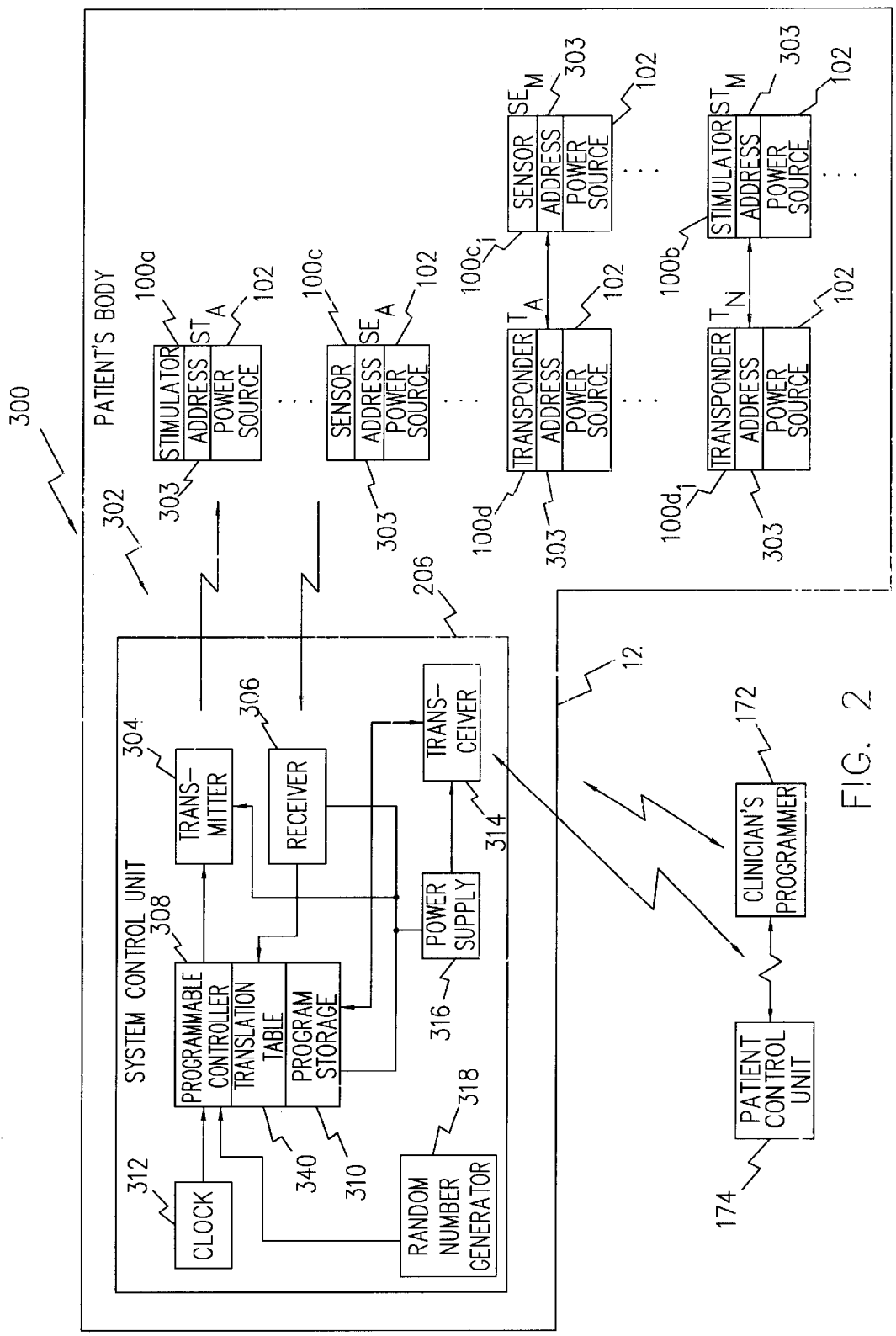
FIG. 2 comprises a block diagram of the system of FIG. 1 showing the functional elements that form the system control unit and implanted microstimulators, microsensors and microtransponders.

FIGS. 1 and 2 show an exemplary system 300 made of implanted devices 100, preferably battery-powered, under control of a system control unit (SCU) 302, preferably also implanted beneath a patient's skin 12. As described in the '284 patent, potential implanted devices 100 (see also the block diagram shown in FIG. 3A) include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes. The sensors, e.g., 100c, can be remotely programmed to sense one or more physiological or biological parameters in the implanted environment of the device, e.g., temperature, glucose level, $O_2$ content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 12 within a patient's body using a hypodermic type insertion tool 176.

As described in the '284 patent, microstimulators and microsensors are remotely programmed and interrogated via a wireless communication link, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication link, each implanted device is manufactured with an address or identification code (ID) 303 specified in address storage circuitry 108 (see FIG. 3A) as described in the '284 patent.

By using one or more such implantable devices in conjunction with the SCU 302 of the present invention, the capabilities of such implanted devices can be further expanded. For example, in an open loop mode (described below in reference to FIG. 4), the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode (described below in reference to FIGS. 5–7), the SCU 302 periodically interrogates one or more microsensors and accordingly adjusts the commands transmitted to one or more microstimulators.

FIG. 2 shows a system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz is used which corresponds to a frequency that freely passes through a typical body's fluids and tissues. However, such sound means that operate at any frequency, e.g., greater than 1 Hz, are also considered to be within the scope of the present invention. Alternatively, the signal transmitter 304 and signal receiver 306 can communicate using modulated AC, e.g., magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication means is used.

Figure 3A:
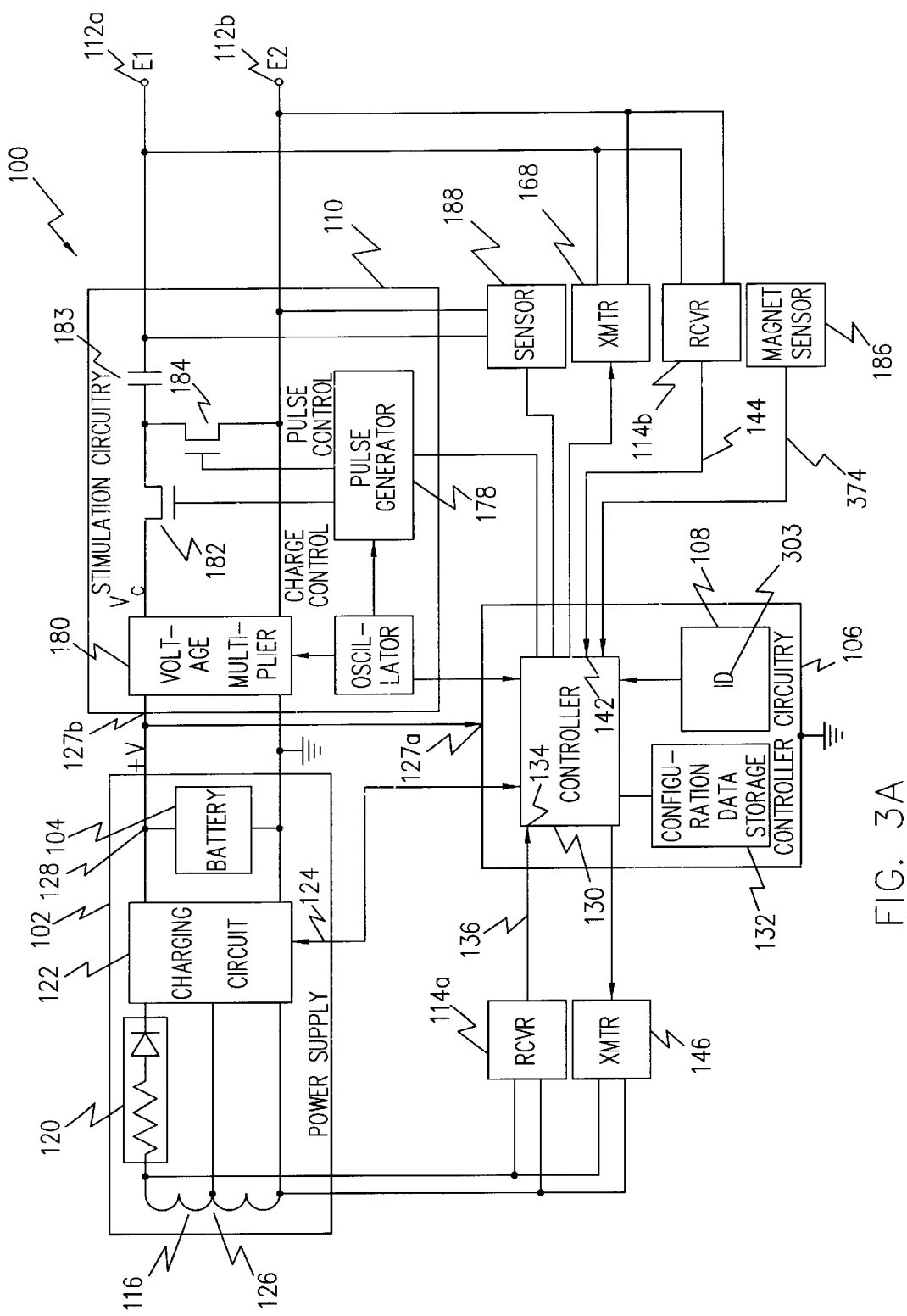
FIG. 3A comprises a block diagram of an exemplary implantable device, as shown in U.S. Pat. No. 6,164,284, including a battery for powering the device for a period of time in excess of one hour in response to a command from the system control unit.
Figure 3B:
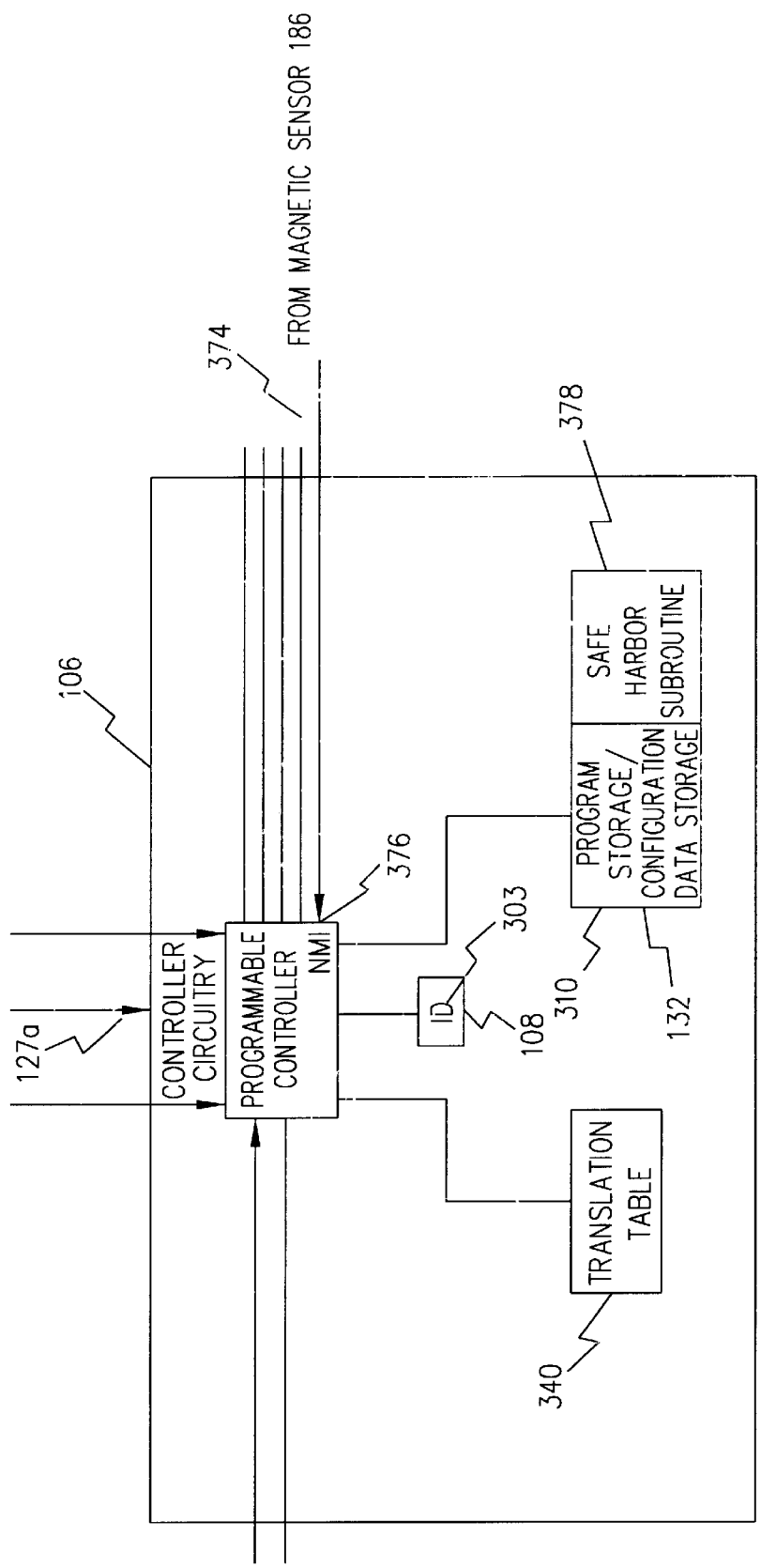
FIG. 3B comprises a simplified block diagram of controller circuitry that can be substituted for the controller circuitry of FIG. 3A, thus permitting a single device to be configured as a system control unit and/or a microstimulator and/or a microsensor and/or a microtransponder.

FIG. 3A comprises a block diagram of an exemplary implantable device 100 operable under control of controller circuitry 106 and includes a battery 104, preferably rechargeable, for powering the device for a period of time in excess of one hour and responsive to command signals from a remote device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 3B shows an alternative implementation of the controller circuitry 106 of FIG. 3A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

In a preferred embodiment, the contents of the program storage 310, i.e., the software that controls the operation of the programmable controller 308, can be remotely downloaded, e.g., from the clinician's programmer 172 using data modulated onto an RF signal or an AC magnetic field. In this embodiment, it is preferable that the contents of the program storage 310 for each SCU 302 be protected from an inadvertent change. Accordingly, the contents of the address storage circuitry 108, i.e., the ID 303, is preferably used as a security code to confirm that the new program storage contents are destined for the SCU 302 receiving the data. This feature is significant if multiple patient's could be physically located, e.g., in adjoining beds, within the communication range of the clinician's programmer 172.

In a further aspect of the present invention, it is preferable that the SCU 302 be operable for an extended period of time, e.g., in excess of one hour, from an internal power supply 316 (see FIG. 2). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body. Accordingly, power supply 102 of FIG. 3A is the preferred power supply 316 for the SCU 302 as well.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 3A), controller 130 commands stimulation circuitry 110 to generate a sequence of drive pulses through electrodes 112 to stimulate tissue, e.g., a nerve or muscle, proximate to the implanted location of the microstimulator, e.g., 100a or 100b. In operation, a programmable pulse generator 178 and voltage multiplier 180 are configured with parameters corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

In a next operational mode, the battery-powered implantable device 100 can be configured to operate as a microsensor, e.g., 100*c*, that can sense one or more physiological or biological parameters in the implanted environment of the device. In accordance with a preferred mode of operation, the system control unit 302 periodically requests the sensed data from each microsensor 100*c* using its ID 303 stored in the address storage circuitry 108, and responsively sends command signals to microstimulators, e.g., 100*a* and 100*b*, adjusted accordingly to the sensed data. For example, sensor circuitry 188 can be coupled to the electrodes 112 to sense or otherwise used to measure a biological parameter, e.g., temperature, glucose level, $O_2$ content, voltage, current, impedance, neural or muscular stimulations/evoked responses, etc., and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is remotely programmable via the device's communication interface.

Additionally, the sensing capabilities of a microsensor preferably include the capability to monitor the battery status via path 124 from the charging circuit 122 and can additionally include using an ultrasonic transducer (not shown) or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system.

In another operational mode, the battery-powered implantable device 100 can be configured to operate as a microtransponder, e.g., 100*d*. In this operational mode, the microtransponder receives (via the aforementioned RCVR 114*a* using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 1) to program/ command the implanted devices 100. However, the magnitude of the emitted signal may not be sufficient to be successfully received by all of the implanted devices 100. As such, a microtransponder 100*d* may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100*c* in a patient's foot. Despite the efficiency of ultrasonic, magnetic and propagated RF communication in a patient's body, such a signal could still be insufficient to pass from a patient's foot to a patient's wrist (the typical location of the patient control unit 174). As such, a microtransponder 100*d* could be implanted (if needed) in the patient's torso to improve the communication link.

Figure 4:
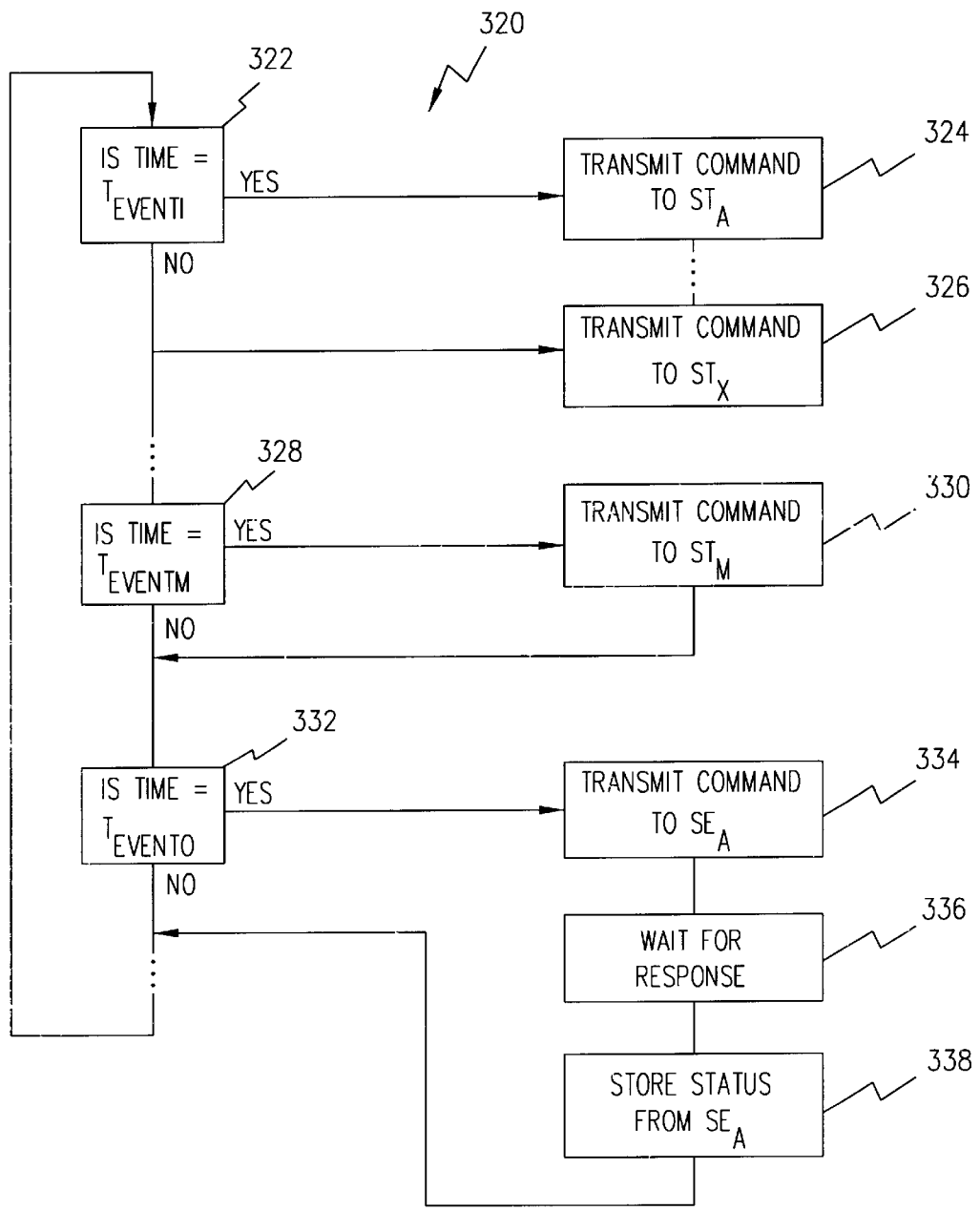
FIG. 4 shows an exemplary flow chart of the use of the exemplary system in an open loop mode for controlling/monitoring a plurality of implanted devices, e.g., microstimulators, microsensors.

FIG. 4 shows a block diagram of an exemplary open loop control program, i.e., a task scheduler 320, for controlling/ monitoring a body function/parameter. In this process, the programmable controller 308 is responsive to the clock 312 (preferably a crystal controlled oscillator to thus permit real time scheduling) in determining when to perform any of a plurality of tasks. In this exemplary flow chart, the programmable controller 308 first determines in block 322 if it is now at a time designated as $T_{EVENT1}$ (or at least within a sampling error of that time), e.g., at 1:00 AM. If so, the programmable controller 308 transmits a designated command to microstimulator A ($ST_A$) in block 324. In this example, the control program continues where commands are sent to a plurality of stimulators and concludes in block 326 where a designated command is sent to microstimulator X ($ST_X$). Such a subprocess, e.g., a subroutine, is typically used when multiple portions of body tissue require stimulation, e.g., stimulating a plurality of muscle groups in a paralyzed limb to avoid atrophy. The task scheduler 320 continues through multiple time event detection blocks until in block 328 it determines whether the time $T_{EVENTM}$ has arrived. If so, the process continues at block 330 where, in this case, a single command is sent to microstimulator M ($ST_M$). Similarly, in block 332 the task scheduler 320 determines when it is the scheduled time, i.e., $T_{EVENTO}$, to execute a status request from microsensor A ($SE_A$). If so, a subprocess, e.g., a subroutine, commences at block 334 where a command is sent to microsensor A ($SE_A$) to request sensor data and/or specify sensing criteria. Microsensor A ($SE_A$) does not instantaneously respond. Accordingly, the programmable controller 308 waits for a response in block 336. In block 338, the returned sensor status data from microsensor A ($SE_A$) is stored in a portion of the memory, e.g., a volatile portion of the program storage 310, of the programmable controller 308. The task scheduler 320 can be a programmed sequence, i.e., defined in software stored in the program storage 310, or, alternatively, a predefined function controlled by a table of parameters similarly stored in the program storage 310. A similar process may be used where the SCU 302 periodically interrogates each implantable device 100 to determine its battery status.

Figure 5:
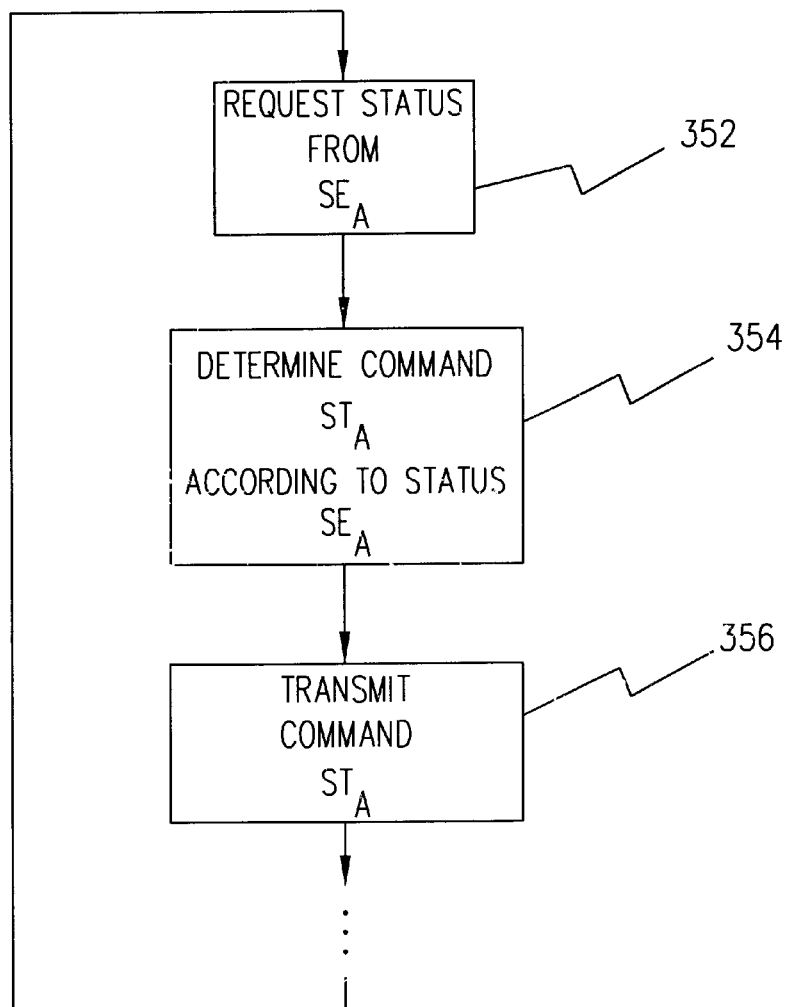
FIG. 5 shows a simplified flow chart of the use of closed loop control of a microstimulator by altering commands from the system control unit in response to status data received from a microsensor.

FIG. 5 is an exemplary block diagram showing the use of the system of the present invention to perform closed loop control of a body function. In block 352, the SCU 302 requests status from microsensor A ($SE_A$). The SCU 302, in block 354, then determines whether the present command given to a microstimulator is satisfactory and, if necessary, determines a new command and transmits the new command to the microstimulator A ($ST_A$) in block 356. For example, if microsensor A ($SE_A$) is reading a voltage corresponding to the degree of contraction resulting from stimulating a muscle, the SCU 302 could transmit a command to microstimulator A ($ST_A$) to adjust the sequence of drive pulses, e.g., in magnitude, duty cycle, etc., and accordingly change the voltage sensed by microsensor A ($SE_A$). Accordingly, closed loop, i.e., feedback, control is accomplished. The characteristics of the feedback (position, integral, derivative (PID)) control are preferably program controlled by the SCU 302 according to the control program contained in program storage 310.

Figure 6:
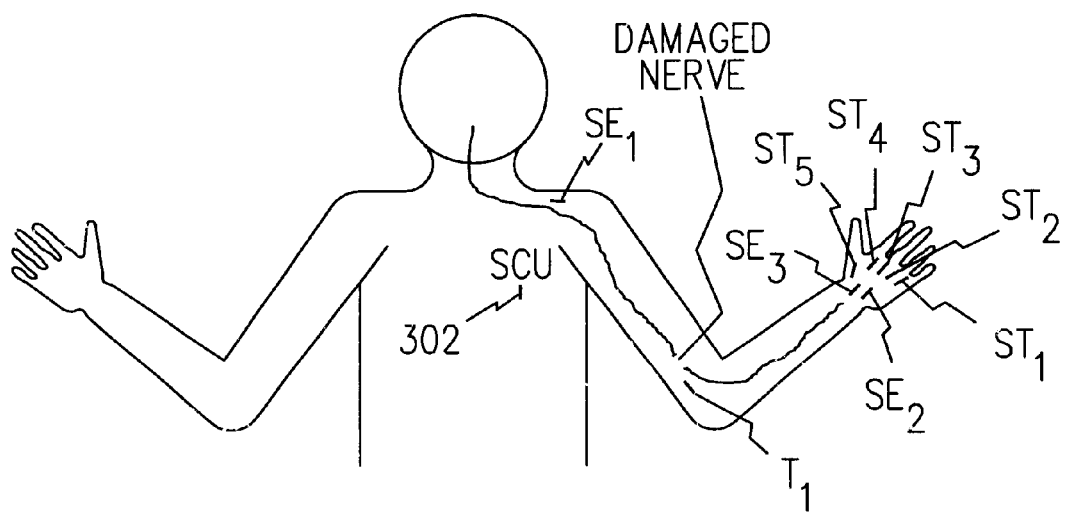
FIG. 6 shows an exemplary injury, i.e., a damaged nerve, and the placement of a plurality of implanted devices, i.e., microstimulators, microsensors and a microtransponder under control of the system control unit for "replacing" the damaged nerve.

FIG. 6 shows an exemplary injury treatable by embodiments of the present system 300. In this exemplary injury, the neural pathway has been damaged, e.g., severed, just above the a patient's left elbow. The goal of this exemplary system is to bypass the damaged neural pathway to permit the patient to regain control of the left hand. An SCU 302 is implanted within the patient's torso to control a plurality of stimulators, $ST_1$–$ST_5$, implanted proximate to the muscles respectively controlling the patient's thumb and fingers (shown in the patient's hand for simplicity). Additionally, microsensor 1 ($SE_1$) is implanted proximate to an undamaged nerve portion where it can sense a signal generated from the patient's brain when the patient wants hand closure. Optional microsensor 2 ($SE_2$) is implanted in a portion of the patient's hand where it can sense a signal corresponding to stimulation/motion of the patient's pinky finger and microsensor 3 ($SE_3$) is implanted and configured to measure a signal corresponding to grip pressure generated when the fingers of the patient's hand are closed. Additionally, an optional microtransponder ($T_1$) is shown which can be used to improve the communication between the SCU 302 and the implanted devices.

Figure 7:
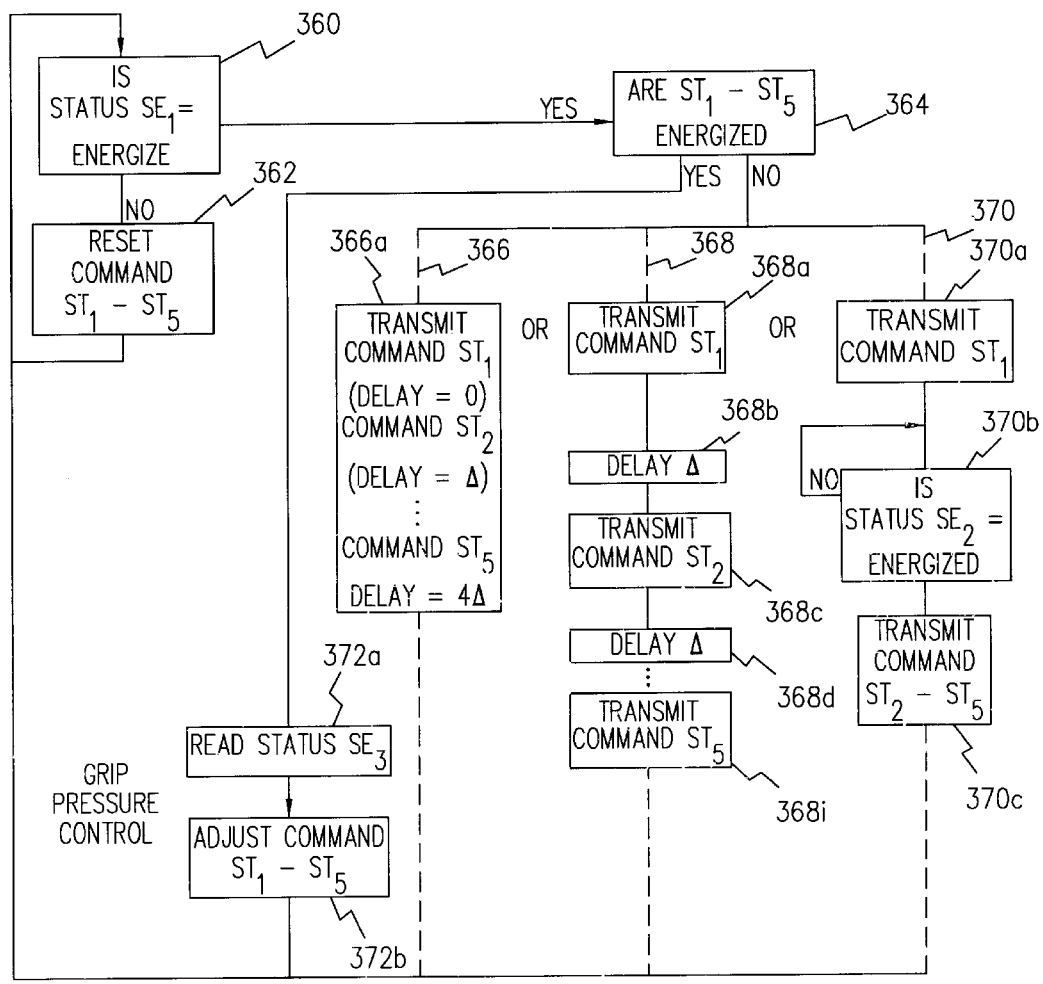
FIG. 7 shows a simplified flow chart of the control of the implanted devices of FIG. 6 by the system control unit.

FIG. 7 shows an exemplary flow chart for the operation of the SCU 302 in association with the implanted devices in the exemplary system of FIG. 6. In block 360, the SCU 302 interrogates microsensor 1 ($SE_1$) to determine if the patient is requesting actuation of his fingers. If not, a command is transmitted in block 362 to all of the stimulators ($ST_1$–$ST_5$) to open the patient's hand, i.e., to de-energize the muscles which close the patient's fingers. If microsensor 1 ($SE_1$) senses a signal to actuate the patient's fingers, the SCU 302 determines in block 364 whether the stimulators $ST_1$–$ST_5$ are currently energized, i.e., generating a sequence of drive/stimulation pulses. If not, the SCU 302 executes instructions to energize the stimulators. In a first optional path 366, each of the stimulators is simultaneously (subject to formatting and transmission delays) commanded to energize in block 366a. However, the command signal given to each one specifies a different start delay time. Accordingly, there is a stagger between the actuation/closing of each finger.

In a second optional path 368, the microstimulators are consecutively energized by a delay Δ. Thus, microstimulator 1 ($ST_1$) is energized in block 368a, a delay is executed within the SCU 302 in block 368b, and so on for all of the microstimulators. Accordingly, paths 366 and 368 perform essentially the same function. However, in path 366 the interdevice timing is performed by the clocks within each implanted device 100 while in path 368, the SCU 302 is responsible for providing the interdevice timing.

In path 370, the SCU 302 actuates a first microstimulator ($ST_1$) in block 370a and waits in block 370b for its corresponding muscle to be actuated, as determined by microsensor 2 ($SE_2$), before actuating the remaining stimulators ($ST_2$–$ST_5$) in block 370c. This implementation could provide more coordinated movement in some situations.

Once the stimulators have been energized, as determined in block 364, closed loop grip pressure control is performed in blocks 372a and 372b by periodically reading the status of microsensor 3 ($SE_3$) and adjusting the commands given to the stimulators ($ST_1$–$ST_5$) accordingly. Consequently, this exemplary system has enabled the patient to regain control of his hand including coordinated motion and grip pressure control of the patient's fingers.

Figure 8:
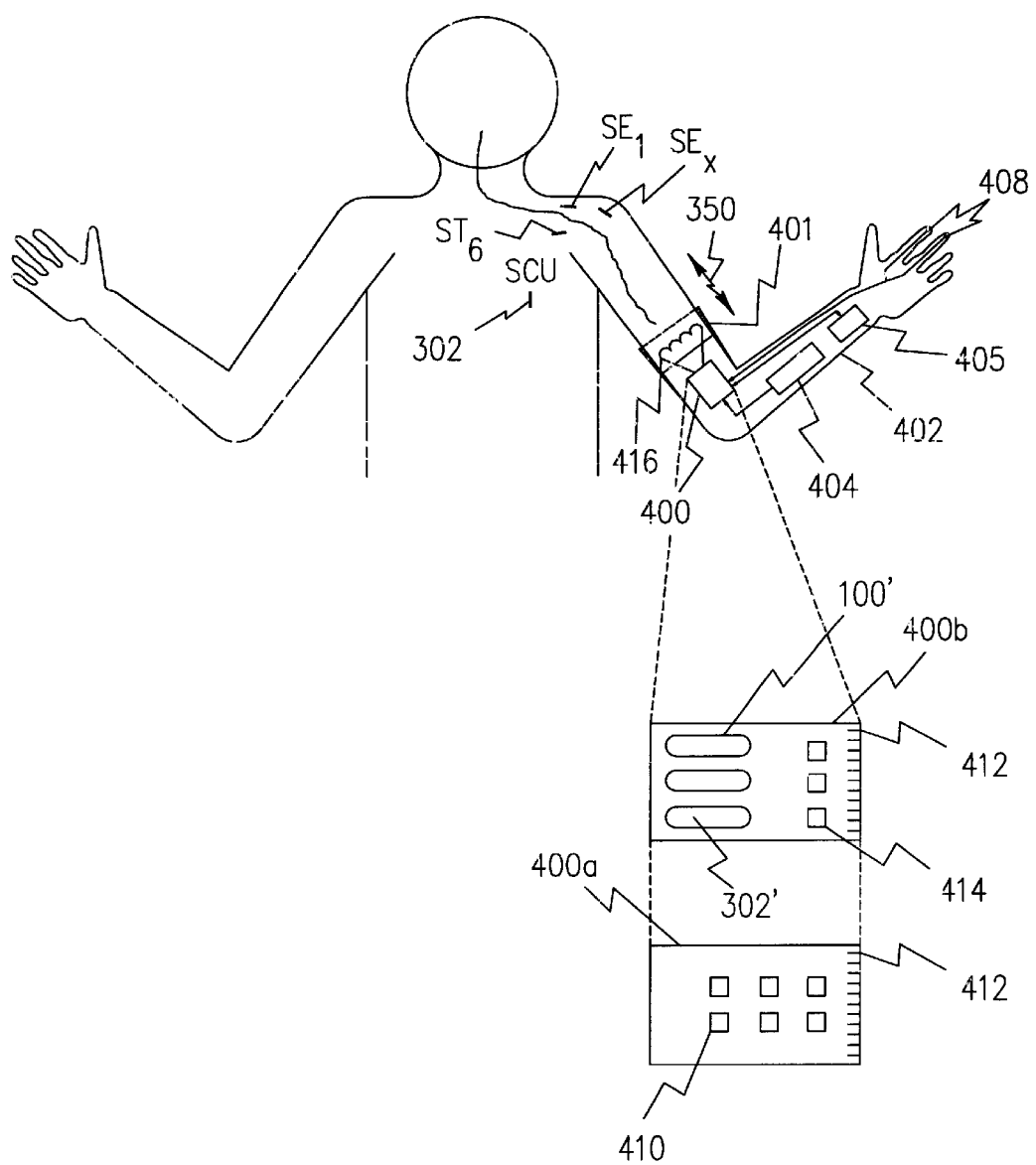
FIG. 8 shows an exemplary application where an absent arm is replaced by a prosthetic arm having motorized control and optional electronic sensing functions and where this prosthetic arm communicates with one or more of the implantable devices.

In reference to FIG. 6, there has been described a system where the implantable devices are used to "replace" or repair a damaged neural pathway. In FIG. 8, a first alternative prosthetic application is described where a body portion, e.g., a limb, is absent due to an injury, a disease that required its amputation, a birth defect, etc. Electromechanical prosthetic devices are known for replacing such an absent limb. Known prosthetic devices typically interface to the patient via pressure sensors/switches or electrical sensors that make contact at the surface of the patient's skin. In the present invention, an electromechanical prosthetic device 402 is physically connected to the patient via conventional means, e.g., cuff 401. However, the control interface is instead provided via a wireless communication link 350 to one or more of the aforedescribed implantable devices, e.g., $SE_1$, SCU, etc. The prosthetic device 402 contains communication/control circuitry 400 (referred to as second communication/control circuitry to contrast with the similarly functioning circuitry within the implantable devices) which operates according to a communication protocol similar/compatible with that used by the implantable devices 100 (see, for example, the circuitry of FIG. 3A, referred to in this context as the first communication/control circuitry). In response to data received from the implantable devices 100, the second communication/control circuitry 400 causes actuator/motor means 406 to move mechanical joints or the like (not shown) in the prosthetic device 402. Preferably, sensor means, e.g., 408 shown at the prosthetic finger tips, within the prosthetic device 402 are used to communicate sensor data, e.g., pressure, temperature, etc., via bi-directional communication link 350 to an implantable stimulation device, e.g., $ST_6$, which stimulates a neural pathway, i.e., a nerve, to provide sensory data back to the patient, thus preferably closing the control loop. Clearly, this is a simplified example of what was already described in reference to FIG. 6. Much of what has been already described in reference to FIG. 6 is equally applicable to the embodiment of FIG. 8. Furthermore, the number of control loops, i.e., control actuators/motors, sensors, and associated implanted microsensors and microstimulators can be increased significantly to improve the amount of patient control/functionality.

Furthermore, it should be noted that in such an environment, an amputee patient may experience "phantom pain" or other distressing sensations from the absent limb. Accordingly, embodiments of the present invention may include implantable microstimulators that are used to block neural pathways to thus eliminate/minimize the "phantom pain".

Depending upon the amount of closed loop control desired, a system control unit (SCU) 302 may be used to integrate control of one or more actuators, e.g., 406, with sensed information from sensors in implantable devices, e.g., $SE_1$–$SE_{609\ X}$, and sensors, e.g., 408, in the prosthetic device 402. The SCU 302 may be comparable in size and form factor to the implantable devices 100 or may be made with a larger form factor to accommodate a larger battery (see U.S. Pat. No. 6,208,894). When the SCU 302 is only used to provide additional control functions, e.g., closed loop control, of the prosthetic device 402, the SCU need not be implanted. In such situations, it is preferable that the SCU, shown as 302' or 302", be located within the prosthetic device 402 and thus may be constructed with different form factor constraints from that of an implantable SCU. However, in situations where the SCU 302 also controls other body parameters, implantation of the SCU 302 is preferred.

Second communication/control circuitry 400 may be implemented in various ways. For example in a first implementation, second communication/control circuitry 400a may be comprised of one or more integrated circuits 410 that operate according to the same communication protocol and perform many of the equivalent functions found in one or more implantable devices 100. Additionally, communication/control circuitry 400 may include the functionality associated with the SCU 302. Typically, this circuitry 400a is somewhat modified or supplemented to enable it to drive and interface to the actuators and/or associated circuitry of the prosthetic device 402 via a connector 412. Preferably, circuitry 400a is maintained in a sealed compartment within the prosthetic device to protect it from the environment.

In a second implementation, second communication/control circuitry 400b is implemented using one or more "implantable" devices 100' (and optionally an SCU 302') supplemented by integrated circuits 414 to provide an interface to the actuators and/or associated circuitry of the prosthetic device 402 via connector 412. While implantable devices 100 and/or the SCU 302 may be used in such an implementation that are identical with aforedescribed hermetically-sealed versions, the hermeticity requirements of these devices in this prosthetic environment are significantly reduced. Accordingly, should such "implantable" devices function properly while not meeting the hermeticity requirements for implantation (a much more severe environment), these devices are still candidates for use in this second implementation. Furthermore, essentially identical devices may be purposely manufactured to lower hermeticity standards (for cost/yield purposes) for use in this prosthetic environment.

Figure 9:
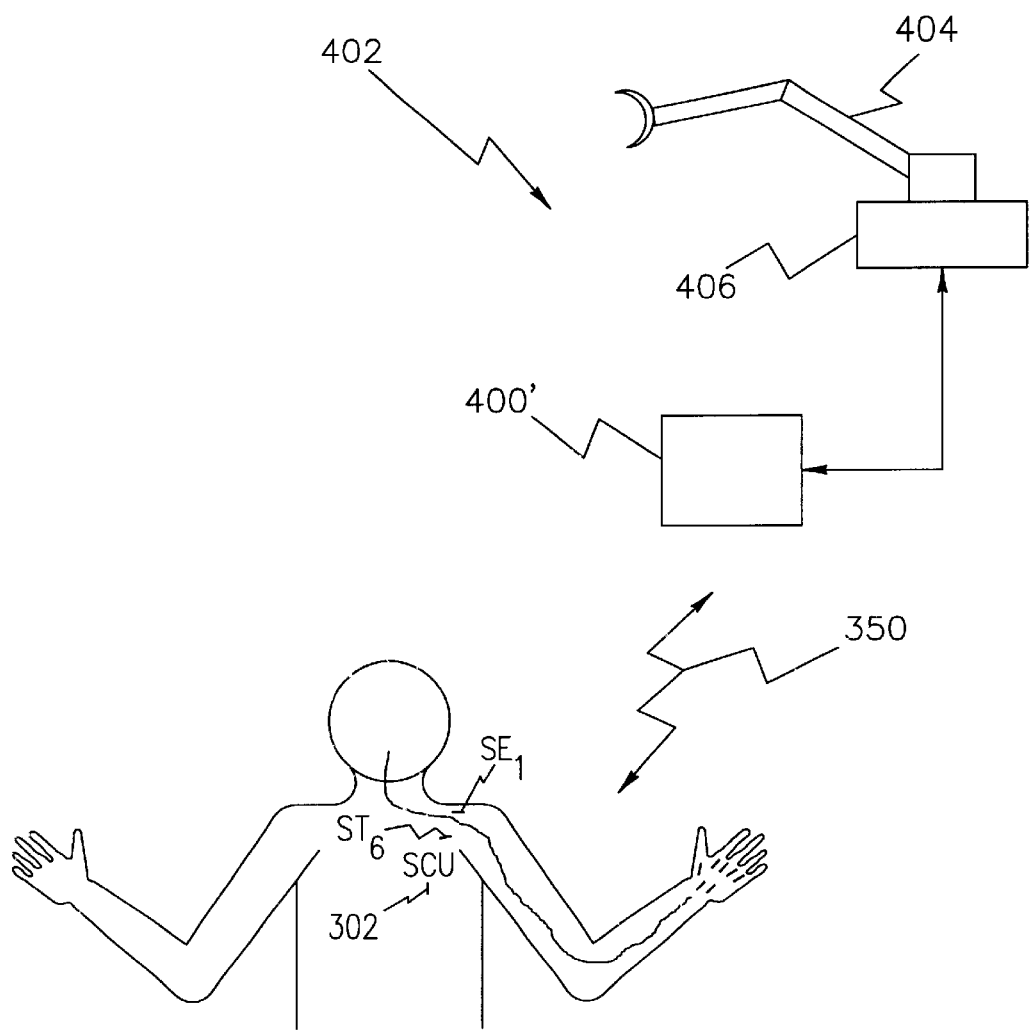
FIG. 9 shows an alternative exemplary application where the prosthetic device is a motorized robotic crane or the like that the user can remotely operate via signals sensed by one or more of the implanted devices on the patient's normally operating neural pathways.

Robert Browning (1812–1889) is credited with the phrase "Ah, but a man's reach should exceed his grasp, or what's a heaven for?" In FIG. 9, a second alternative prosthetic application is shown that demonstrates how an embodiment of the present invention can accomplish this goal. In certain hostile or physically stressful environments, e.g., operating a crane on a space shuttle, defusing a bomb, etc., it may be desirable for a user to directly use his arms, fingers, other appendages, via operational neural pathways to interact with a prosthetic/robotic device; thus, increasing the amount of control dexterity available with the robotic device and preserving safety. In this context, any electromechanical system is considered to be a prosthetic device. Thus, crane 404 is controlled by electromechanical actuator/motor means 406 which in turn receives commands and/or provides sensory status information to communication/control circuitry 400'. Communication/control circuitry 400' in turn communicates via bidirectional communication link 350 to one or more microsensors, e.g., $SE_1$, $SE_2$, $SE_3$, etc., microstimulators, e.g., $ST_6$, or an SCU that are implanted within the patient's body.

While the invention herein disclosed has been described by means of specific embodiments and applications thereof, numerous modifications and variations could be made thereto by those skilled in the art without departing from the scope of the invention. For example, while the present invention has been primarily described in reference to a battery-powered implantable device as described in reference to the '284 and '452 patents, the present invention is equally applicable to use with an RF-powered implantable device as described in U.S. Pat. Nos. 5,193,539 and 5,193,540. As opposed to the aforedescribed battery-powered implantable devices, such RF-powered devices require essentially "constant" power from an external coil in order for them to operate. The exemplary battery-powered devices of the '284 and '452 patents free up the patient from carrying an external apparatus for supplying power. However, in embodiments of the present invention (see the embodiment of FIG. 8), an external apparatus, i.e., the prosthetic device 402, is present whenever the implantable devices need power to operate. Accordingly, since the actuators/motors in a typical prosthesis need a significantly larger amount of power than the referenced implantable devices and since the typical prosthesis needs to be self-powered (e.g., by a battery 405, preferably rechargeable, e.g., by a portion of circuitry 400), a small portion of that power can be electromagnetically supplied through a coil 416 and powered by the power source 405 in the prosthesis 402, e.g., under control of a portion of the second communication/control circuitry 400, to "constantly" supply power to RF-powered implantable devices, e.g., as found in the '539 and '540 patents. Alternatively, in a system using battery-powered implantable devices, the coil 416 would only be energized periodically, e.g., to supply power as needed to recharge the rechargeable battery in the battery-powered implantable device. Of course, systems that include both RF-powered and battery-powered implantable devices are also considered to be within the scope of the present invention. Furthermore, applicable prosthetic devices could also include one or more micro electromechanical systems (MEMS) or nanomachines that are implanted within the patient's body as long as such devices communicate, preferably via a wireless communication channel, with one or more of the implantable devices. Finally, the control loops, generally described so far, control responses in the prosthetic device 402 under control of an SCU 302, preferably implanted, and/or one or more implanted devices 100. Such a control loop may be referred to as a macro level of control. However, one or more sets of communication/control circuitry 400 may, alternatively, be configured to generated a localized, reflex (i.e., a micro level of control) response to locally sensed information, e.g., temperature, pressure, etc., while, preferably still providing the aforementioned macro level of control through additional devices, e.g., the SCU 302 and/or one or more implantable devices 100. Such embodiments are considered to be within the scope of the present invention. It is therefore to be understood that the invention may be practiced otherwise than as specifically described herein.

What is claimed is:

1. A method for controlling a prosthetic device in response to neural pathway signals, said method comprising the steps of:

forming one or more implantable devices contained within sealed elongate housings in a patient's body, wherein each said sealed housing has an axial dimension of less than 60 mm and a lateral dimension of less than 6 mm and includes at least two electrodes integral with and on opposing ends of said housing, whereby said housings are suitable for injection into the patient's body and said implantable devices are configured for monitoring or affecting at least one neural pathway of the patient's body via said electrodes in response to a first communication/control circuitry mounted within said housings;

forming an externally locatable prosthetic device having one or more actuators for controlling and sensors for monitoring one or more aspects of said prosthetic device, whereby said prosthetic device additionally comprises a second communication/control circuitry compatible with said first communication/control circuitry for controlling and sensing aspects of said prosthetic device in response to signals received from one or more of said implantable devices;

coupling said prosthetic device to said patient's body; and periodically communicating in a closed loop manner between said first communication/control circuitry in said one or more implantable devices and said second communication/control circuitry in said prosthetic device according to unique predefined identification addresses specified in address storage circuitry of each of said implantable devices that determine which of said implantable devices respond to received signals from said prosthetic device, said prosthetic device receiving commands corresponding to one or more sensed neurological signals from one or more of said implantable devices and said one or more implantable devices receiving sensed signals from said prosthetic device.

2. The method of claim 1 whereby said implantable devices at least periodically require externally provided electromagnetic energy to provide operating power to said implantable devices and said prosthetic device includes an energy source and circuitry for driving a coil to deliver said required electromagnetic energy, said method additionally including the step of periodically energizing said coil to provide operating power to one or more of said implantable devices.

3. The method of claim 1 whereby at least one of said implantable devices requires externally provided electromagnetic energy to provide operating power to said implantable device and said prosthetic device includes an energy source and circuitry for driving a coil to deliver said required electromagnetic energy, said method additionally including the step of energizing said coil to provide operating power to one or more of said implantable devices.

4. The method of claim 1 whereby at least one of said implantable devices periodically requires externally provided electromagnetic energy for charging a rechargeable battery located within said implantable device to provide operating power to said implantable device and said prosthetic device includes an energy source and circuitry for driving a coil to deliver said required electromagnetic energy, said method additionally including the step of periodically energizing said coil to provide operating power to one or more of said implantable devices.

5. The method of claim 1 additionally comprising the step of implanting a system control unit within said patient's body wherein said system control unit communicates with said first communication/control circuitry within said housings and said second communication/control circuitry within said prosthetic device in order to provide supervisory closed loop control.

6. The method of claim 1 additionally comprising the step of implanting a system control unit within said prosthetic device wherein said system control unit communicates with said first communication/control circuitry within said housings and said second communication/control circuitry within said prosthetic device in order to provide supervisory closed loop control.

7. The method of claim 1 wherein said step of forming a prosthetic device with second communication/control circuitry compatible with said first communication/control circuitry comprises forming said second communication/control circuitry from circuitry essentially functionally identical to said first communication/control circuitry.

8. The method of claim 1 wherein said step of forming a prosthetic device with second communication/control circuitry compatible with said first communication/control circuitry comprises forming said second communication/control circuitry from one or more devices essentially identical with said implantable devices.

9. A system for controlling a prosthetic device in response to neural pathway signals, said system comprising:

one or more implantable devices configured for implantation within a patient's body, wherein each said implantable device is contained within a sealed elongate housing having an axial dimension or less than 60 mm and a lateral dimension of less than 6 mm and includes at least two electrodes integral with and on opposing ends of said housing, whereby said housings are suitable for injection into the patient's body and said implantable devices are configured for monitoring or affecting at least one neural pathway of the patient's body via said electrodes in response to a first communication/control circuitry mounted within said housings and responsive to a unique predefined identification address for each of said implantable devices; and an externally locatable prosthetic device having one or more actuators for controlling and sensors for monitoring one or more aspects of said prosthetic device, whereby said prosthetic device additionally comprises a second communication/control circuitry compatible with said first communication/control circuitry for controlling and sensing aspects of said prosthetic device in response to signals received from said one or more implantable devices, wherein said first communication control circuitry in said one or more implantable devices and said second communication control circuitry in said prosthetic device periodically communicate in a closed loop manner according to said unique predefined identification addresses specified in address storage circuitry of each of said implantable devices that determine which of said implantable devices respond to received signals from said externally locatable prosthetic device wherein said prosthetic device receives commands corresponding to one or more sensed neurological signals from one or more of said implantable devices and said one or more implantable devices receives sensed signals from said prosthetic device.

10. The system of claim 9 wherein:

selected ones of said one or more said implantable devices obtain operating power from externally provided electromagnetic energy; and said prosthetic device additionally comprises:
a power source;
a coil for providing electromagnetic energy; and
driver circuitry for providing an electrical signal to said coil to cause it to emit electromagnetic energy to thereby provide operating power to said selected implantable device.

11. The system of claim 5 wherein:

selected ones of said one or more said implantable devices contain:
a rechargeable battery for providing operating power;
a coil for periodically receiving externally provided electromagnetic energy; and
charging circuitry for using said periodically provided electromagnetic energy received by said coil to charge said rechargeable battery; and said prosthetic device additionally comprises:
a power source;
a coil for periodically providing electromagnetic energy; and
driver circuitry for periodically providing an electrical signal to said coil to cause it to emit electromagnetic energy to thereby charge said rechargeable batteries in said selected implantable devices.

12. The system of claim 11 wherein said power source within said prosthetic device is rechargeable.

13. The system of claim 9 whereby said first and second communication/control circuitry communicate with each other via a wireless communication link.

14. The system of claim 13 whereby said wireless communication link uses radio frequency communication.

15. The system of claim 9 whereby said prosthetic device is configured for physical coupling to the patient's body.

16. The system of claim 9 whereby said second communication/control circuitry is essentially functionally identical with said first communication/control circuitry.

17. The system of claim 9 whereby said prosthetic device includes one or more of said implantable devices mounted within to perform the function of at least a portion of said second communication/control circuitry.

18. The system of claim 9 additionally comprising a system control unit for communicating with one or more of said implantable devices and said second communication/control circuitry in said prosthetic device and to thereby supervise the interaction of said prosthetic device and one or more of said implantable devices in a closed loop manner.

19. The system of claim 18 wherein said system control unit is configured for implantation within the patient's body.

20. The system of claims 18 wherein said prosthetic device includes said system control unit.

21. The system of claim 18 wherein said prosthetic device comprises at least one sensing device and one actuator responsive in part thereto to enable a reflex response.

22. The system of claim 21 wherein said prosthetic device comprises two or more of sets of said second communication/control circuitry essentially identical with said first communication control circuitry for providing said reflex response.

23. A system for providing closed loop control of an externally locatable electromechanical device having one or more actuators and one or more transducers in response to neural pathway signals, said system comprising:
one or more implantable devices configured for implantation within a patient's body and including at least two electrodes, whereby said implantable devices are suitable for injection into the patient's body and said devices are configured for monitoring or affecting at least one neural pathway of the patient's body via said electrodes in response to a first communication/control circuitry mounted within said implantable devices and responsive to a unique predefined identification address for each of said implantable devices; and
an externally locatable electromechanical device having one or more actuators for controlling and transducers for monitoring one or more aspects of said externally locatable electromechanical device, whereby said externally locatable electromechanical device additionally comprises a second communication/control circuitry compatible within said first communication/control circuitry for controlling and sensing aspects of said externally locatable electromechanical device in response to signals received from said one or more implantable devices, wherein said first communication/control circuitry in said one or more implantable devices and said second communication/control circuitry in said externally locatable electromechanical device periodically communicate in a closed loop manner according to said unique predefined identification addresses specified in address storage circuitry of each of said implantable devices that determine which of said implantable devices respond to received signals from said externally locatable electromechanical device wherein said externally locatable electromechanical device receives commands corresponding to one or more sensed neurological signals from one or more of said implantable devices and said one or more implantable devices receives sensed signals from said externally locatable electromechanical device.

24. The system of claim 23 wherein:
selected ones of said one or more said implantable devices obtain operating power from externally provided electromagnetic energy; and
said externally locatable electromechanical device additionally comprises:
a power source;
a coil for providing electromagnetic energy; and
driver circuitry for providing an electrical signal to said coil to cause it to emit electromagnetic energy to thereby provide operating power to said selected implantable device.

25. The system of claim 23 wherein:
selected ones of said one or more said implantable devices contain:
a rechargeable battery for providing operating power;
a coil for periodically receiving externally provided electromagnetic energy; and
charging circuitry for using said periodically provided electromagnetic energy received by said coil to charge said rechargeable battery; and
said externally locatable electromechanical device additionally comprises:
a power source;
a coil for periodically providing electromagnetic energy; and
driver circuitry for periodically providing an electrical signal to said coil to cause it to emit electromagnetic energy to thereby charge said rechargeable batteries in said selected implantable devices.

26. The system of claim 25 wherein said power source within said externally locatable electromechanical device is rechargeable.

27. The system of claim 26 additionally comprising a system control unit for communicating with one or more of said implantable devices and said second communication/control circuitry in said externally locatable electromechanical device and to thereby supervise the interaction of said externally locatable electromechanical device and one or more of said implantable devices in a closed loop manner.

28. The system of claim 27 wherein said system control unit is configured for implantation within the patient's body.

29. The system of claim 27 wherein said externally locatable electromechanical device includes said system control unit.

30. The system of claim 26 wherein said externally locatable electromechanical device comprises at least one sensing device and one actuator responsive in part thereto to enable a reflex response.

31. The system of claim 30 wherein said externally locatable electromechanical device comprises two or more of sets of said second communication/control circuitry essentially identical with said first communication control circuitry for providing said reflex response.

32. The system of claim 23 whereby said first and second communication/control circuitry communicate with each other via a wireless communication link.

33. The system of claim 32 whereby said wireless communication link uses radio frequency communication.

34. The system of claim 23 whereby said externally locatable electromechanical device is a prosthetic device configured for physical coupling to the patient's body.

35. The system of claim 23 whereby said externally locatable electromechanical device is configured for operation remote from the patient's body.

36. The system of claim 23 whereby said second communication/control circuitry is essentially functionally identical with said first communication/control circuitry.

37. The system of claim 23 whereby said externally locatable electromechanical device includes one or more of said implantable devices mounted within to perform the function of at least a portion of said second communication/control circuitry.

* * * * *

UNITED STATES PATENT AND TRADEMARK OFFICE
CERTIFICATE OF CORRECTION

PATENT NO.    : 6,695,885 B2
DATED         : February 24, 2004
INVENTOR(S)   : Schulman et al.

It is certified that error appears in the above-identified patent and that said Letters Patent is hereby corrected as shown below:

Title page,
Item [75], Inventors, should read as follows:

-- [75]  Inventors:  Joseph H. Schulman, Santa Clartia, CA (US);
         Yitzhak Zilberman, Santa Clarita, CA (Israel);
         Lee J. Mandell, West Hills, CA (US); Robert D. Dell, Valencia, CA (US); John C. Gord, Venice, CA (US) --.

Column 14,
Line 59, should read as follows: -- The system of claim 9 wherein: --

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,695,885 B2
DATED : February 24, 2004
INVENTOR(S) : Schulman et al.

It is certified that error appears in the above-identified patent and that said Letters Patent is hereby corrected as shown below:

Column 14,
Line 14, should read as follows -- gate housing having an axial dimension of less than 60 --

Signed and Sealed this

Fifteenth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,695,885 B2
DATED : February 24, 2004
INVENTOR(S) : Schulman et al.

It is certified that error appears in the above-identified patent and that said Letters Patent is hereby corrected as shown below:

Title page,
Item [62], Related U.S. Application Priority Data, to read as follows:

--[60]   Continuation-in-part of application No. 09/677,384, filed on Sep. 30, 2000, now Pat. No. 6,564,807, which is a division of application No. 09/048,827, filed on Mar. 25, 1998, now Pat. No. 6,164,284, which is a continuation-in-part of application No. 09/030,106, filed on Feb. 25, 1998, now Pat. No. 6,185,452.--

Column 1,
Lines 6-18, to read as follows:

--This application is a continuation-in-part of U.S. patent application Ser. No. 09/677,384, filed Sep. 30, 2000, now U.S. Pat. No. 6,564,807. U.S. Pat. No. 6,564,807 is a divisional of U.S. patent application Ser. No. 09/048,827, filed Mar. 25, 1998, now U.S. Pat. No. 6,164,284. U.S. Pat. No. 6,164,284 is a continuation-in-part of U.S. patent application Ser. No. 09/030,106, filed Feb. 25, 1998, now U.S. Pat. No. 6,185,452, and claims the benefit of U.S. Provisional Application No. 60/042,447, filed Mar. 27, 1997. U.S. Pat. No. 6,185,452 claims the benefit of U.S. Provisional Application No. 60/039,164, filed Feb. 26, 1997. Furthermore, the present application claims the benefit of U.S. Provisional Application No. 60/300,397, filed Jun. 22, 2001.--

Signed and Sealed this

Fifteenth Day of February, 2005

JON W. DUDAS
*Director of the United States Patent and Trademark Office*